United States Patent [19]

Mattson et al.

[11] Patent Number: 4,826,843
[45] Date of Patent: May 2, 1989

[54] CEREBRAL FUNCTION ENHANCING DIAZINYLPIPERIDINE DERIVATIVES

[75] Inventors: Ronald J. Mattson, Meriden; Joseph P. Yevich, Southington; Michael S. Eison, Avon, all of Conn.

[73] Assignee: Bristol-Myers, New York, N.Y.

[21] Appl. No.: 90,985

[22] Filed: Aug. 28, 1987

Related U.S. Application Data

[63] Continuation-in-part of Ser. No. 868,468, May 30, 1986, abandoned, which is a continuation-in-part of Ser. No. 753,006, Jul. 8, 1985, abandoned.

[51] Int. Cl.$^4$ .................. C07D 401/14; A61K 31/445; A61K 31/505; A61K 31/50
[52] U.S. Cl. ..................................... 514/252; 514/253; 514/269; 514/273; 514/274; 514/275; 514/256; 544/238; 544/320; 544/321; 544/327; 544/329; 544/332; 544/336; 544/408; 544/409; 544/311; 544/312; 544/316; 544/317
[58] Field of Search ............... 544/335, 238, 320, 334, 544/311, 312, 321, 327, 329, 316, 317, 408, 409; 514/253, 269, 274, 256, 253, 273, 275, 252

[56] References Cited

U.S. PATENT DOCUMENTS

| | | | |
|---|---|---|---|
| 3,717,634 | 2/1973 | Wu et al. | 260/256.4 |
| 4,423,049 | 12/1983 | Temple | 424/251 |
| 4,524,206 | 6/1985 | New et al. | 544/230 |
| 4,668,687 | 5/1987 | Yevich et al. | 514/252 |

OTHER PUBLICATIONS

Butler, et al., *J. Med. Chem.*, 27, pp. 684–691 (1984) (3/13).
Malawska, et al., *Polish Journal of Pharmacology*, 34, pp. 373–382 (1982) (5/4).

*Primary Examiner*—John M. Ford
*Attorney, Agent, or Firm*—Richard P. Ryan

[57] ABSTRACT

A series of diazinylpiperidine compounds of Formula I

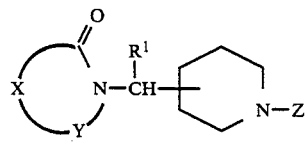

wherein X is an ethylene chain or a 1,2-benzo ring; Y is carbonyl or methylene; $R^1$ is hydrogen or lower alkyl; and Z is an $R^2$, $R^3$-disubstituted diazinyl ring selected from pyridazine, pyrimidine, and pyrazine ring systems. Pharmacologic and neuroanatomical testing demonstrates that compounds of the series act to enhance cerebral function in mammals, particularly when there is a deficit in normal cerebral functioning. Specific pharmacologic test results indicate that compounds of Formula I possess cognition and memory enhancing activity.

36 Claims, No Drawings

CEREBRAL FUNCTION ENHANCING DIAZINYLPIPERIDINE DERIVATIVES

CROSS REFERENCE TO RELATED APPLICATION

This is a continuation-in-part application of Ser. No. 868,468 filed May 30, 1986, now abandoned, which is itself a continuation-in-part application of Ser. No. 753,006 filed July 8, 1985, and now abandoned.

BACKGROUUND OF THE INVENTION

This invention generally pertains to heterocyclic carbon compounds having drug and bio-affecting properties and to their preparation and use. In particular, the invention is concerned with disubstituted piperidine derivatives wherein one substituent is a cyclic amide or imide ring linked by a bridging methylene moiety to one of the carbon ring positions of the piperidine ring and the other substituent is a diazinyl ring system attached to the piperidine nitrogen atom. The compounds of this invention are cerebral function enhancers useful in treatment of various dementias due to degenerative process as well as in enhancing memory and learning.

Clinical aspects of various degenerative dementias as well as the socioeconomic problems they cause in affected populations are well known to those skilled in the art. One will also appreciate that various drug treatments of these disorders are currently under study. Among such drugs are a class of drugs known as nootropic agents or, more commonly, cognition enhancers; some of which are currently undergoing clinical evaluation in patients diagnosed as having Alzheimer's disease, a serious and fairly common CNS disorder of the elderly. Chemically, these drugs under clinical study are members of a class of N-substituted 2-pyrrolidinone derivatives of structure 1.

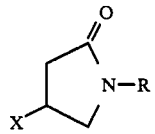

a: $X=H$; $R=-CH_2CONH_2$ (piracetam)
b: $X=OH$; $R=-CH_2CONH_2$ (oxiracetam)
c: $X=H$; $R=-CH_2CONH[CH_2]_2N[CH(CH_3)_2]_2$ (pramiracetam)

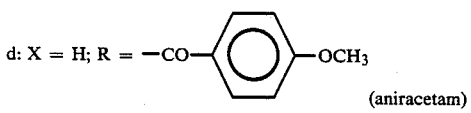

d: $X=H$; $R=-CO-\langle\text{phenyl}\rangle-OCH_3$ (aniracetam)

For a representative reference describing the testing and properties of a member of this series 1, see Butler, et al., *J. Med. Chem.*, 27, pp. 684–691 (1984). Preliminary clinical results with this class of agents, exemplified by structures 1a-d, indicate that these drugs may have some beneficial effects in treating senile dementias in the elderly.

Related art may be viewed in light of the following general structural formula 2

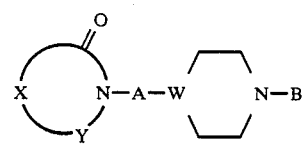

in which X is $C_{2-4}$ alkylene or a 1,2-benzo ring; Y is carbonyl or methylene; A is a bridging moiety such as alkylene, alkanoyl, alkyleneamidoalkylene, and the like; W is nitrogen or CH; and B is an aryl or pyrimidinyl ring system. The most closely related art is that disclosed and claimed in our U.S. Pat. No. 4,668,687 issued May 26, 1987. The subject matter relates to a series of formula 2 compounds wherein W is nitrogen. The closest related compounds disclosed in U.S. Pat. No. 4,668,687 may be characterized by structural formula 3.

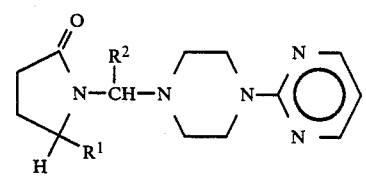

wherein $R^1$ is hydrogen or lower alkyl; and $R^2$ can also be hydrogen or lower alkyl. As can be seen, these earlier compounds are structurally distinguishable from the instant series of compounds on the basis of chemical structure as these earlier compounds are piperazine ring derivatives ($W=N$ in Formula 2) whereas the instant compounds are piperidine ring derivatives ($W=CH$ in Formula 2).

Other subject matter related to formula 3 compounds has been disclosed by Malawska, et al., in "Synthesis and Pharmacological Properties of Some 2-Pyrrolidinone Mannich Bases" in the *Polish Journal of Pharmacology*, 1982, 34, 373-382. They describe a series of compounds, of which one subclass is represented by structural formula 4, which reportedly display analgesic properties as well as weak anti-inflammatory action,

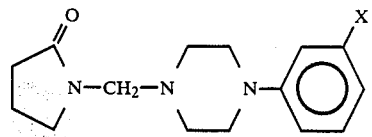

wherein X is hydrogen or chlorine.

A large number of psychotropic compounds with structures corresponding to formula 2 wherein Y is carbonyl, W is nitrogen, and A is $C_{2-3}$ alkylene have been disclosed by Wu, Temple, New, and their co-workers and others. These compounds are comprised of cyclic imide rings, e.g. succinimides, glutarimides, phthalimides, etc. The shortest linkage defined by A in these compounds is ethylene as compounds wherein A is methylene are too unstable, particularly in acidic media, for practical usage. For more detailed disclosure of these compounds, see: Wu, et al., U.S. Pat. Nos. 3,717,634 patented Feb. 20, 1973; Temple, U.S. Pat. Nos. 4,423,049 patented Dec. 27, 1983; and New and Yevich, 4,524,206 patented June 18, 1985.

Increasing structural departure from compounds of the instant invention is found in other art cited in our above-referenced patent. In summary, the instant diazinylpiperidine compounds described herein are structurally novel cerebral function enhancing agents and there are no teachings in the art which would make the specific compounds comprising this invention anticipated or obvious.

SUMMARY OF THE INVENTION

A series of compounds of structural Formula I

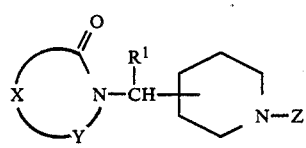

wherein X is an ethylene chain or a 1,2-benzo ring; Y is carbonyl or methylene; $R^1$ is hydrogen or lower alkyl; and Z is an $R^2$, $R^3$-disubstituted diazinyl ring selected from pyridazine, pyrimidine, and pyrazine ring systems. $R^2$ and $R^3$ are independently chosen from hydrogen, lower alkyl, lower alkoxy, lower alkylthio, cyano, trifluoromethyl and halogen. Compounds of this series can be incorporated into pharmaceutical compositions for use in enhancing cerebral function. Specific applications intended include restoration of cerebral function in dementias due to degenerative processes; amnesia reversal; and improvement in memory and learning processes.

DETAILED DESCRIPTION OF THE INVENTION

In its broadest aspect, the present invention is concerned with 1-(4-diazinyl)piperidinyl derivatives of N-methylene cyclic amides and imides having psychocognitive properties and being characterized by structural Formula I.

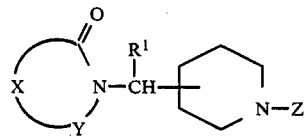

In Formula I, X is a $C_2$ (ethylene) alkylene chain or a 1,2-benzo ring connecting Y and the carbonyl group to give, e.g. when Y is also carbonyl, a phthalimide moiety. Y is a carbonyl group (but only when X is a 1,2-benzo ring) or $CH_2$. In Formula I, $R^1$ can be either hydrogen or lower ($C_{1-4}$) alkyl; and Z is an $R^2$, $R^3$-disubstituted diazinyl ring selected from pyridazine, pyrimidine, and pyrazine ring systems, with $R^2$ and $R^3$ being independently chosen from hydrogen, lower alkyl, lower perfluoroalkyl (such as trifluoromethyl or pentafluoroethyl), lower alkoxy, lower alkylthio, cyano, and halogen. By lower alkyl is meant that these groupings contain from 1 to 4 carbon atoms. Halogen means F, Cl, Br, or I. For preferred compounds, X is ethylene, Y is methylene, $R^1$ is hydrogen, and $R^2$ and $R^3$ are selected from hydrogen, trifluoromethyl, and halogen, with the most preferred halogen being chloride.

It is to be understood that the present invention is considered to include the various stereoisomers, e.g. optical isomers including individual enantiomers, mixtures of enantiomers, diastereomers, and mixture of diastereomers, which can arise as a consequence of structural asymetry due to the presence of one or two asymetric carbon atoms which may be incorporated in some compounds of the instant series. Separation of the individual isomers is accomplished by application of various methods which are well known to practitioners in the art. For medicinal use, the pharmaceutically acceptable acid addition salts, those salts in which the anion does not contribute significantly to toxicity or pharmacological activity of the organic cation may be preferred in some cases. The acid addition salts are obtained either by reaction of an organic base of structure I with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, pamoic acid, cyclamic acid, pivalic acid, and the like; useful inorganic acids are hydrohalide acids such as HCl, HBr, HI; sulfuric acids; phosphoric acids; and the like. Additionally, the present invention also encompasses any of the Formula I compounds existing in solvate form such as a hydrate.

The compounds of the instant invention can be conveniently prepared by means of a general process which is shown in Scheme 1.

Scheme 1
General Synthetic Process

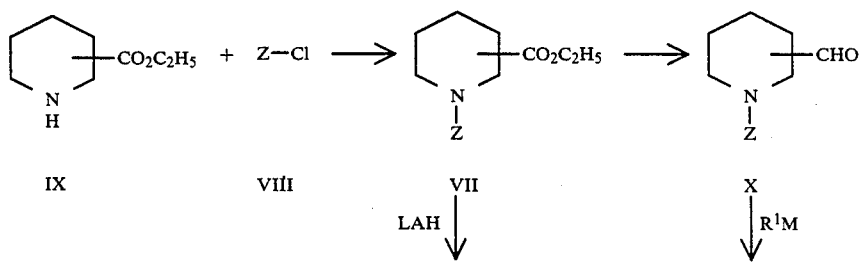

Scheme 1
General Synthetic Process

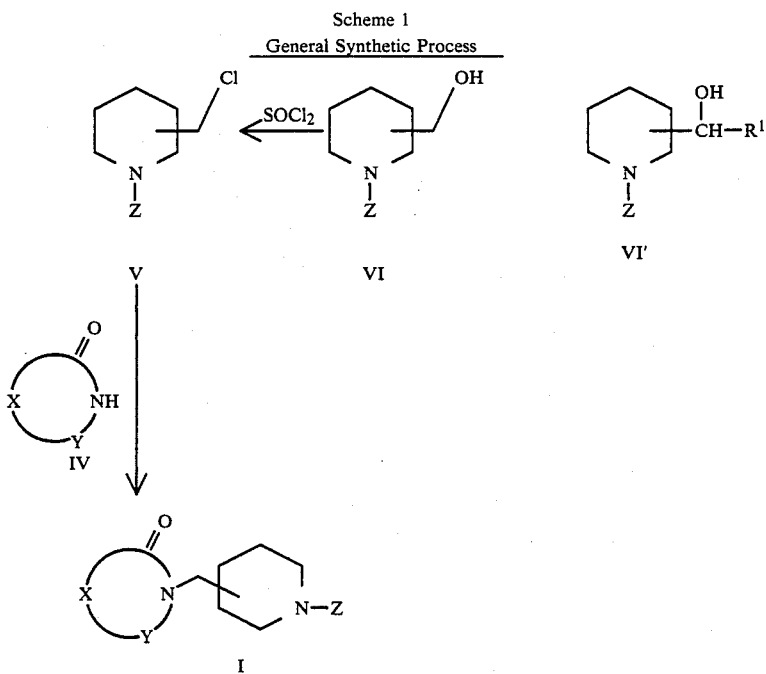

In Scheme 1, the symbols X, Y, and Z are as previously defined. Basically, a piperidine carboxylate ester (IX) is coupled with an appropriate diazine halide (VIII). While an ethyl ester and a chloride group are shown in compounds IX and VIII, respectively, in Scheme 1; other equivalent groups, e.g. another alkyl carboxylate ester and/or a different halogen may be used. These alterations would be familiar to an organic chemist skilled in synthesis of compounds. Typically, the reaction of IX and VIII will take place in a reaction solvent such as acetonitrile in the presence of a base such as potassium carbonate, thereby giving the product (VII). The VII product may either be reduced with lithium aluminum hydride in an appropriate solvent such as tetrahydrofuran to give reaction intermediate VI ($R^1$=H) or, alternatively, VII may be converted to the aldehyde X using standard methods for ester transformation into an aldehyde moiety, and this followed by treatment with an organo metallic reagent, $R_1M$ (wherein M represents the appropriate metal cation or Grignard complex) to give the intermediate product VI'. The primary alcohol intermediate (VI) or secondary alcohol (VI') is treated with thionyl chloride to give the corresponding chloro compound (V) which is then coupled with a selected cyclic amide or imide (IV) to give the desired product of Formula I. This coupling reaction proceeds similarly to that of IX and VIII with a preferred reaction solvent in this case being dimethylformamide and incorporating a base such as potassium carbonate. It will be understood by those skilled in the art that other conversions of VI intermediates may be made which would effectively convert the hydroxy group into a different leaving group (e.g. a tosylate or mesylate moiety) in order ot facilitate alkylation of the nitrogen atom in the cyclic amid/imide compound.

Another process may be utilized to produce products of Formula I and this process is set forth as Scheme 2.

Scheme 2
Synthetic Process When X is an Ethylene Chain

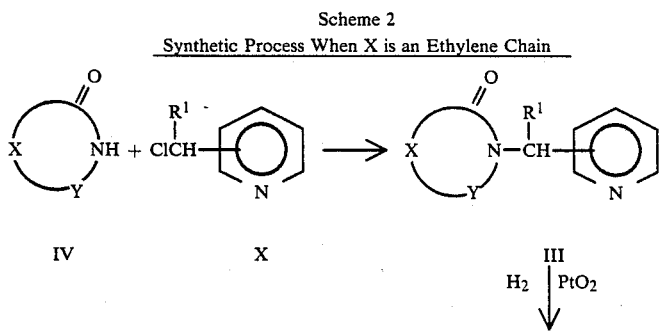

Scheme 2
Synthetic Process When X is an Ethylene Chain

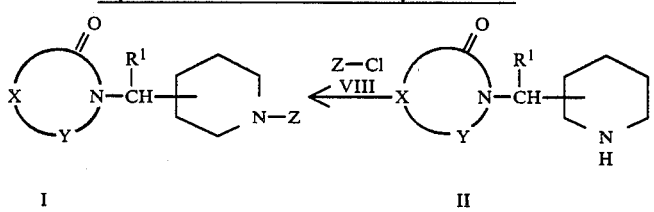

In Scheme 2, $R^1$, X, Y, and Z are as previously defined. While the process outlined in Scheme 2 generally produces products of Formula I in higher yields than the general process of Scheme 1, it does not have the general applicability of Scheme 1. Because of the catalytic reduction (conversion of III to II) only cyclic amides/imides impervious to catalytic reduction may be used. For example, when X is a 1,2-benzo ring, e.g. IV is phthalimide, the benzo ring moiety is subsequently reduced to a 1,2-cyclohexyl derivative, thereby giving a hexahydrophthalimide ring system.

To summarize the foregoing, there is described a process for the preparation of a compound of Formula I

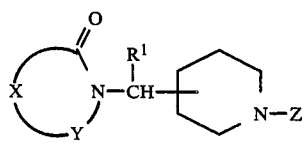     I wherein $R^1$, X, Y, and Z are as previously defined. This process comprises selection of a process from the group of processes consisting of (a) (1) coupling compounds IX and VIII

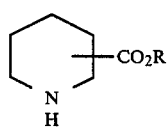     IX

Z—Q     VIII wherein R is a $C_{1-6}$ alkyl group and Q is a suitable displacement group such as chloride, bromide, iodide, sulfate, phosphate, tosylate, mesylate, or the like to give an intermediate product of Formula VII;

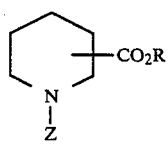     VII (2) treating the intermediate product, VII, with the metallic reagent $R^1M$, wherein M is the appropriate metalloid ion or complex, e.g. lithium aluminum hydrido or Grignard reagent complex, to give the reaction intermediate of Formula VI;

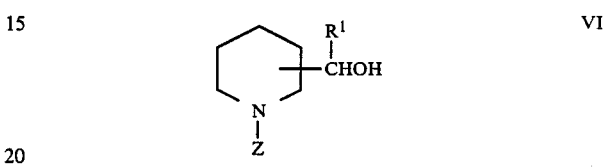     VI (3) treating intermediate VI with an appropriate reagent to convert the OH group of VI to a leaving group Q in the compound of Formula V;

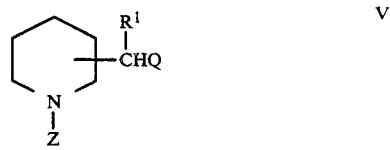     V and
(4) reacting intermediate V with a cyclic amide/imide compound of Formula IV,

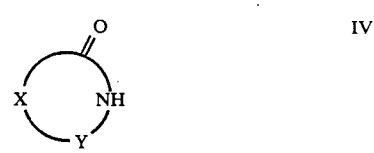     IV to give a product of Formula I;
(b) (1) reacting a cyclic amide/imide compound of Formula IV,

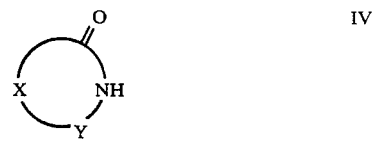     IV wherein X is not 1,2-benzo ring, with a pyridine intermediate of Formula X

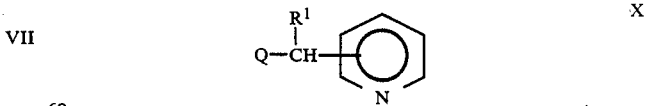     X to give the intermediate compound of Formula III;

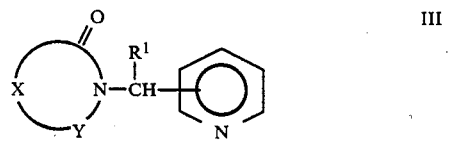     III (2) catalytically reducing the compound of Formula III to give the piperidine intermediate compound of Formula II

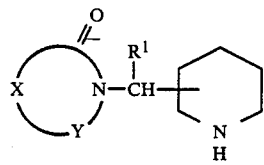

and (3) coupling the compound of Formula II with compound Z-Q to give a product of Formula I.

Compounds of the instant invention have been evaluated for cerebral function enhancing activity using as a primary screen the reversal of electroconvulsive shock-induced amnesia for a step-down passive avoidance response (cf: Banfis, et al., *J. Pharmacol. Meth.*, 8, 255 (1982); Janvik, *Ann. Rev. Psychol.*, 23, 457 (1972); and, McGaugh and Petrinovich, *Int. Rev. Neurobiology*, 8 139 (1965)). Reference compounds such as pramiracetam, piracetam, aniracetam, etc., having activity in this paradigm have been purported to affect memory processes and may be useful in treating various dementias due to degenerative processes or diseases such as Alzheimer's disease. In this test, 12 animals are administered drugs and 30 minutes later are trained to remain immobile to avoid foot shock. Immediately following the training, the animals are given electroconvulsive shock. Twenty-four hours later the animals are tested for retention of the learned behavior; and any animal which remains on the platform for 300 seconds without stepping down is considered to have retained the passive avoidance response. Two groups of control animals are used for comparison: group-1 receives vehicle with electroconvulsive shock and the group-2 receives vehicle with sham-electroconvulsive shock. A test compound is considered active at a given dosage level if the mean latency to step-down is both statistically greater than the value for the electroconvulsive shock control group (placebo control group-1) and not statistically different from the value for the sham-electroconvulsive shock control group-2.

A test compound is considered to have intermediate activity at a given dosage level if results for the drug group are statistically different from both control groups. For the sake of comparison, all drugs were tested after subcutaneous administration; however, preferred compounds of the instant series exhibit activity following oral administration that is little changed from the results following subcutaneous administration of drug. In this regard the following compounds are particularly preferred: 1-[[1-(2-pyrimidinyl)-4-piperidinyl]-methyl]-2-pyrrolidinone, 1-[[1-(2-chloro-4-pyrimidinyl)-4-piperidinyl]methyl]-2-pyrrolidinone, 1-[[1-(6-chloro-2-pyrazinyl)-4-piperidinyl]methyl]-2-pyrrolidinone and, 1-[[1-(2-trifluoro-methyl-4-pyrimidinyl) -4-piperidinyl]methyl]-2-pyrrolidinone. Maintenance of comparable levels of potency in going from subcutaneous to oral administration is a considerable dosing advantage and distinguishes the instant compounds from agents described in prior art references. Additionally, the instant compounds are not labile in acidic media which is another advantage in their manufacture, formulating, shipping and storage, as well as for dosing.

Selected preferred compounds have undergone additional behavioral testing in animal models such as assessing drug effects on the acquisition of radial arm maze performance and a food foraging task in rats. In this latter behavioral test, selected preferred compounds enhanced the rate at which animals with disrupted CNS function (lesions of the nucleus basalis) acquired a food foraging task.

The effects of selected preferred compounds in young and old rat brain on glucose utilization were also studied. These studies involved the use of labeled deoxyglucose and standard autoradiographic measurements of brain slices. Such methods are well described in the scientific literature and would be familiar to any practitioner skilled in the pertinent art. Results of such testing demonstrates that the selected compounds reverse age-related changes in glucose utilization in old rat brains such that the resultant metabolic activity pattern closely resembles that seen in healthy young rats.

Consideration of test results obtained for compounds of the present invention indicate their usefulness in several specific applications wherein such psychocognitive enhancement or normalizing effects on cerebral function would be highly desireable. The subject compounds are intended to be useful in treatment of dementias due to degenerative processes, diseases, and the like; with some specific examples being age-related memory dysfunction; AIDS-related dementia; multiple infarct dementia; Alzheimer's disease; Parkinson-related dementia; and the like. Similarly, the compounds are useful in enhancement of memory and learning processes and for acquisition of new information as well as treating deficits such as those encountered in benign senescent forgetfulness, learning disabilities and certain retardation states, e.g. minimal brain dysfunction. The compounds are also useful as antiamnesiacs and would find applicaion against amnesias whether induced by ECS (a standard antidepressant treatment); drugs, e.g. benzodiazepines, alcohol, etc.; or trauma, e.g. head injury, post-neurosurgery, and so forth. Other uses which are envisioned for the compounds of this invention would be to treat miscellaneous disorders such as dyslexia, aphasia, and Tourette's syndrome.

In addition to the usefulness of the compounds of Formula I as cognition enhancing agents or mild stimulants of neuronal activity, the compounds have been found to be useful in preventing amnesia which results from electroconvulsive shock. Such activity not only relates to memory retention in normal aging and senility processes but would be useful in protecting against the amnesia-producing effects of electroconvulsant shock as it is used clinically. Electroconvulsant shock is employed to treat some classes of psychiatric patients, particularly depressed patients who are refractory to traditional pharmacologic therapy. It is well documented that these electroconvulsant shock treatments induce the undesirable side-effect of amnesia in those patients to whom it is administered. The instant compounds which exhibit activity in protecting against the amnesia-producing effects of electroconvulsant shock in pharmacologic testing would be useful adjuncts to the clinical use of electroconvulsant shock in psychiatric treatment.

In summary of the foregoing discussion, the instant compounds have cerebral function enhancing properties particularly suited to their use in treating dementias cognition and memory enhancement, reversal and/or prevention of amnesia and certain miscellaneous applications. Thus, another aspect of the instant invention concerns a process for enhancing cerebral function in a mammal in need of such treatment which comprises systemic administration to such mammal of an effective dose of a Formula I compound or a pharmaceutically acceptable acid addition salt thereof. The administration and dosage regimen of compounds of Formula I is considered to be done in the same manner as for the reference compound piracetam, cf: Reisberg, et al., in *Drug Development Research,* 2475-480 (1982); Weng, et al., in *Rational Drug Therapy,* 17(5), 1-4 (1983); Reisberg, etw al., in "Psychopathology in the Aged", Editors, Cole and Barrett, Raven Press, New York, pages 243-245 (1980) and pramiracetam, cf: Butler, et al., *J. Med. Chem.,* 27, pp 684-691 (1984).

Although the dosage and dosage regimen must in each case be carefully adjusted, utilizing sound professional judgment and considering the age, weight and condition of the recipient, the route of administration and the nature and extent of mental deterioration, generally, the daily dose will be from about 0.1 g to about 10 g, preferably 0.5 g to 5 g, when given orally. In some instances, a sufficient therapeutic effect can be obtained at lower doses while in others, larger doses will be required. As is apparent to one skilled in clinical pharmacology, the amount of Formula I compound comprising the daily dose may be given in a single or divided dose, taking into account those principles understood by the skilled practitioner and necessary for his practice of the art.

The term "systemic administration" as used herein refers to oral, sublingual, buccal, nasal, dermal, rectal, intramuscular, intravenous, and subcutaneous routes. Generally, it will be found that when a compound of the present invention is administered orally which is the preferred route, a slightly larger quantity of the active drug may be required to produce the same effect as a somewhat smaller quantity when given parenterally. In accordance with good clinical practice, it is preferred to administer the instant compounds at a concentration level which will produce effective beneficial effects without causing any harmful or untoward side effects.

Therapeutically, the instant compounds are generally given as pharmaceutical compositions comprised of an effective cerebral function enhancing amount of a compound of Formula I or a pharmaceutically acceptable acid addition salt thereof and a pharmaceutically acceptable carrier. Pharmaceutical compositions for effecting such treatment will contain a major or minor amount (e.g. from 95% to 0.5%) of at least one compound of the present invention in combination with a pharmaceutical carrier, the carrier comprising one or more solid, semi-solid, or liquid diluent, filler and formulation adjuvant which is non-toxic, inert and pharmaceutically acceptable. Such pharmaceutical compositions are preferably in dosage unit forms; i.e., physically discrete units having a pre-determined amount of the drug corresponding to a fraction or multiple of the dose which is calculated to produce the desired therapeutic response. In usual practice, the dosage units contain 1, ½, ⅓, or less of a single dose. A single dose preferably contains an amount suffieient to produce the desired therapeutic effect upon administration at one application of one or more dosage units according to the pre-determined dosage regimen, usually a whole, half, third, or less of the daily dosage adinistered once, twice, three, or more times a day. It is envisioned that other therapeutic agents can also be present in such a composition. Pharmaceutical compositions which provide from 0.1 to 1 g of the active ingredient per unit dose are preferred and are conventionally prepared as tablets, lozenges, capsules, powders, aqueous or oily suspensions, syrups, elixirs, and aqueous solutions. Preferred oral compositions are in the form of tablets, capsules, and may contain conventional excipients such as binding agents. (e.g., syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from about 0.1% to 10% by weight of the active compound in water or a vehicle consisting of a polyhydric aliphatic alcohol such as glycerine, propylene glycol, and the polyethylene glycols or mixtures thereof. The polyethylene glycols consist of a mixture of non-volatile, usually liquid, polyethylene glycols which are soluble in both water and organic liquids and which have molecular weights from about 200 to 1500.

Description of Specific Embodiments

The compounds which constitute this invention and their methods of preparation as well as their biological activity will appear more fully from a consideration of the following examples which are given for the purpose of illustration only and are not to be construed as limiting the invention in sphere or scope. All temperatures are understood to be in degrees C. when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton (PMR) spectral data corresponds to the number of hydrogen atoms of a particular functional type in the molecule. The nature of the shift as to multiplicity is reported as broad singlet (bs), singlet (s), multiplet (m), doublet (d), doublet of doublet (dd), triplet (t), or quartet (q). Abbreviations employed are DMSO-$d_6$ (perdeuterodjmethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using potassium bromide (KBr) as diluent. All compounds gave satisfactory elemental analysis.

EXAMPLE 1

2-[[1-(2-Pyrimidinyl)-4-piperidinyl]-methyl]-1H-isoindole-1,3-(2H)-dione

This synthetic sequence exemplifies the more general synthesis outlined in Scheme 1, supra.

A. Ethyl 1-(2-Pyrimidinyl)piperidine-4-carboxylate (VIII).—A mixture of ethyl isonipecotate (IX; 31.44 g, 0.2 mole), 2-chloropyrimidine (VIII; 22.91 g, 0.2 mole), and potassium carbonate (27.69 g, 0.2 mole) in acetonitrile (250 mL) was refluxed for 24 hours. The mixture was filtered and the filtrate concentrated in vacuo. The residue was distilled (130-170° at 0.32 Torr.) to give 44.1 g (94%) of product in the form of a clear oil.

B. 4-Hydroxymethyl-1-(2-pyrimidinyl)piperidine (VI).—A solution of the ester (VII; 20 g, 0.085 mole) in tetrahydrofuran (200 mL) was cooled to 0-5° and lithium aluminum hydride (3.23 g, 0.085 mole) was slowly added over a 10 minute period. The mixture was stirred at room temperature for 30 minutes. The excess LAH was quenched with acetone and the mixture diluted by adding 3.2 mL of water followed by 3.2 mL of 15% sodium hydroxide solution and then 9.7 mL of water. The resulting mixture was filtered and the filtrate concentrtted in vacuo to give an oil which was distilled to give 15 g (91%) of a clear oil product, b.p. 140°-190° at 0.3 Torr.

C. 4-Chloromethyl-1-(2-pyrimidinyl)piperidine (V).—A solution of the hydroxymethyl compound (VI; 7.73 g, 0.04 mole) in methylene chloride (40 mL) was cooled to 0°-5° and thionyl chloride (25 mL) was added slowly. The solution was stirred for 12 hours at ambient temperature and then concentrated in vacuo. The residue was dissolved in methylene chloride, extracted with aqueous sodium bicarbonate, and the methylene chloride layer concentrated in vacuo. The residue was chromatographed on silica gel using ethyl acetate as the eluent to give 7.7 g (91%) of product as an oil.

D. Reaction of Intermediate V and Phthalimide.—A mixture of potassium carbonate (2.76 g, 0.02 mole), phthalimide (1.47 g, 0.01 mole), and 4-chloromethyl-1-(2-pyrimidinyl)piperidine (V; 2.12 g, 0.01 mole) in dimethylformamide (50 mL) was heated to about 50° for 24 hours. The dimethylformamide solvent was removed in vacuo and the residue was dissolved in acetone and filtered. The filtrate was concentrated in vacuo to give the crude product which was chromatographed on silica gel using 30% ethyl acetate-hexane as the eluent. The product was then recrystallized from ethyl acetate to yield 0.95 g (20.5%) of product in the form of white crystals, m.p. 109°-111°.

Anal. Calcd. for $C_{18}H_{18}N_4O_2$: C,67.06; H, 5.64; N, 17.38. Found: C, 66.95; H, 5.68; N, 17.17.

NMR (CDCl$_3$): 1.35 (2,m); 1.74 (2,m); 2.10 (1,m); 2.85 (2,m); 3.61 (2,d, 7.0 Hz); 4.76 (2,m); 6.40 (1,t, 4.8 Hz); 7.79 (4,m); 8.27 (2,d, 4.8 Hz).

IR (KBr): 730, 800, 1360, 1400, 1515, 1540, 1590, 1710, 1750, and 2930 cm$^{-1}$.

EXAMPLE 2

1-[[1-(Pyrimidinyl)-4-piperidinyl]methyl]-2-pyrrolidinone

This experimental sequence exemplifies the synthetic process that can be used when X of the Formula I compound is an alkylene chain (see Scheme 2, supra.)

A. 1-[(4-Piperidinyl)methyl]-2-pyrrolidinone Hydrochloride Hydrate (II).—A solution of 1-(4-pyridinylmethyl)-2-pyrrolidinone hydrochloride (III; 15.05 g, 0.0707 mole; prepared from 2-pyrrolidinone and 4-pyridinylmethyl chloride), HCl (10 mL of an 8N solution in absolute ethanol) and absolute ethanol (100 mL) was hydrogenated at 60 psi with PtO$_2$ (1.0 g) for 72 hours. The mixture was filtered and the filtrate reduced in vacuo to give a white solid. The crude product was recrystallized from isopropanol to give 13.03 g (83%) of product as a white powder, m.p. 212°-214°.

B. Reaction of Intermediate Compound II With 2-Chloropyrimidine.—A mixture of the piperidinylmethylpyrrolidinone (II; 5.08 g, 0.0232 mole), 2-chloropyrimidine (2.67 g, 0.0233 mole) and potassium carbonate (7.09 g, 0.0513 mole) in dimethylformamide (60 mL) was heated in a 50-100° oil bath for 14 hours. The mixture was cooled and filtered. The solvent was then removed in vacuo and the residue chromatographed on silica gel using an ethyl acetate-acetone mixture as the eluent to give 4.7 g (78%) of product as white crystals, m.p. 144°-147°.

Anal. Calcd. for $C_{14}H_{20}N_4O$: C, 64.59; H, 7.74; N, 21.52. Found: C, 64.26; H, 7.78; N, 21.20.

NMR (CDCl$_3$): 1.29 (2,m); 1.71 (2,m); 2.01 (3,m); 2.34 (2,t, 7.4 Hz); 2.84 (2,m); 3.16 (2,3, 7.0 Hz); 3.39 (2,t, 6.8 Hz); 4.73 (2,m); 6.40 (1,t, 4.7 Hz); 8.26 (2,d, 4.7 Hz).

IR (KBr): 800, 1360, 1440, 1515, 1540, 1585, 1675, and 2930 cm$^{-1}$.

EXAMPLE 3

1-[[1-(2-Chloro-4-pyrimidinyl)-4-piperidinyl]methyl]-2-pyrrolidinone

A mixture of 1-[(4-piperidinyl)methyl]-2-pyrrolidinone hydrochloride (II, prepared above in Example 2A; 20.1 g, 0.922 mole), 2,4-dichloropyrimidine (14.90 g, 0.1 mole), sodium carbonate (26.5 g, 0.25 mole), and 200 mL dimethylformamide was stirred for 14 hours at room temperature and then heated to 70° for one hour. The mixture was filtered and concentrated in vacuo. The crude residue was chromatographed on silica using ethyl acetate/methanol (95:5) as the eluent thereby separating the product residue into two components. The major component was obtained as 16 g (59%) of off-white powder, m.p. 110-114, and represented the desired 2-chloro-4-pyrimidinyl isomer.

Anal. Calcd. for $C_{14}H_{19}ClN_4O$: C, 57.04; H, 6.50; N, 19.01. Found: C, 56.73; H, 6.44; N, 18.97.

NMR (CDCl$_3$): 1.30 (2,m); 1.78 (2,m); 2.03 (3,m); 2.39 (2,t, 7.4 Hz); 2.92 (2,m); 3.17 (2,d, 7.0 Hz); 3.40 (2,t, 6.8 Hz); 4.35 (2,m); 6.39 (1,d, 6.0 Hz); 7.98 (1,d, 6.0 Hz).

IR (KBr): 965, 1150, 1350, 1360, 1490, 1590, 1685, 2860, and 2950 cm$^{i-1}$.

EXAMPLE 4

1-[[1-(4-Chloro-2-pyrimidinyl)]-4-piperidinyl]methyl]-2-pyrrolidinone

The other isomer, the 4-chloro-2-pyrimidinyl compound, was the smaller component obtained by chromatography and recrystallization from ethyl acetate of the reaction product of Example 3 (above) to give 1.1 g (4%) of white crystals, m.p. 143.5°-145.5°.

Anal. Calcd. for $C_{14}H_{19}ClN_4O$: C, 56.04; H, 6.50; N, 19.01. Found: C, 56.66; H, 6.49; N, 19.81.

NMR (CDCl$_3$) 0.902.1 (5,m); 2.25 (2,t, 5 Hz); 2.75 (2,t, 8 Hz); 3.10 (2,d, 5 Hz); 3.30 (2,t, 5 Hz); 4.5-4.8 (2,d); 6.45 (1,d, 4 Hz); 8.13 (1,d, 4 Hz).

IR (KBr): 1275, 1350, 1419, 1512, 1588, and 1688 cm$^{-1}$.

EXAMPLE 5

1-[[1-(6-Chloro-2-pyrazinyl)-4-piperidinyl]methyl]-2-pyrrolidinone

Using the procedure described above in Examples 2 and 3, a mixture of 1-[(4-piperidinyl)methyl]-2-pyrrolidinone hydrochloride (II, 12.5 g, 0.0556 mole); 2,6-dichloropyrazine (8.37 g, 0.0556 mole); potassium carbonate (19.2 g, 0.139 mole); and DMF (150 mL) was stirred at room temperature for 14 hours and then heated to 70° for one hour. The mixture was filtered and the filtrate concentrated in vacuo. The crude product was recrystallized twice from ethyl acetate to provide 11.16 g (68%) of tan crystals, m.p. 139°-142°.

Anal. Calcd. for C₁₄H₁₉ClN₄O: C, 57.04; H, 6.50; N, 19.01. Found: C, 57.02; H, 6.40; N, 19.03.

NMR (CDCl₂): 1.34 (2,m); 1.77 (2,m); 2.05 (3,m); 2.40 (2,t, 7.2 Hz); 2.91 (2,m); 3.18 (2,d, 7.0 Hz); 3.40 (2,t, 6.8 Hz); 4.30 (2,m); 7.74 (1,s); 7.96 (1,s).

IR (KBr): 835, 1140, 1275, 1415, 1460, 1490, 1500, 1565, 1685, 2840, and 2945 cm⁻¹.

EXAMPLE 6

1-[[1-[2-(Trifluoromethyl)-4-pyrimidinyl]-4-piperidinyl]methyl]-2-pyrrolidinone

Using the procedure described above in Examples 2 and 3, a mixture of 1-[(4-piperidinyl)methyl]-2-pyrrolidinone hydrochloride (II, 21.85 g, 0.1 mole) and sodium carbonate (26.5 g, 0.25 mole) in methanol (150 mL) was refluxed for one hour. The methanol was then removed in vacuo, and acetonitrile (150 mL) was added to the residue. The mixture was cooled and stirred as 4-chloro-2-(trifluoromethyl)pyrimidine (18.28 g, 0.2 mole) was added. The mixture was stirred at room temperature for 18 hours and then filtered and the filtrate concentrated in vacuo to give a thick residue which solidified upon being washed with hexane (100 mL). The light tan powder (23.8 g, 73%) which resulted was chromatographed (5% methanol/ethyl acetate on silica) to give 19.8 g as white crystals, m.p. 118.5°–120.5°.

Anal. Calcd. for C₁₅H₁₉F₃N₄O: C, 54.87; H, 5.83; N, 17.07. Found: C, 54.50; H, 5.86; N, 16.80.

In similar manner a number of additional compounds of Formula I were prepared and are tabulated in Table I.

TABLE 1

Compounds of Formula I

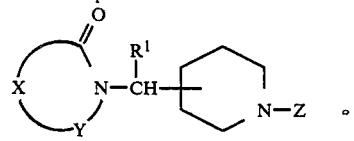

| Ex. | R¹ | X | Y | Piperidine Ring-link | Z | Formula* | m.p. (°) |
|---|---|---|---|---|---|---|---|
| 7 | H | —C₂H₄— | CH₂ | 3- | pyrimidinyl | C₁₄H₂₀N₄O | 105.5–107.5 |
| 8 | H | —C₂H₄— | CH₂ | 2- | pyrimidinyl | C₁₄H₂₀N₄O | 110–113 |
| 9 | H | —C₂H₄— | CH₂ | 4- | 6-chloropyridazinyl | C₁₄H₁₉ClN₄O | 138–139.5 |
| 10 | H | —C₂H₄— | CH₂ | 4- | 5-fluoro-6-(methylthio)pyrimidinyl | C₁₅H₂₁FN₄OS | 96–100 |
| 11 | H | —C₂H₄— | CH₂ | 4- | 5-fluoropyrimidinyl | C₁₄H₁₉FN₄O | 134–136 |
| 12 | H | —C₂H₄— | CH₂ | 4- | 4,6-dichloropyrimidinyl | C₁₄H₁₈Cl₂N₄O | 140–144 |
| 13 | H | —C₂H₄— | CH₂ | 4- | dichloropyrimidinyl | C₁₄H₁₈Cl₂N₄O | 111–114.5 |

TABLE 1-continued

Compounds of Formula I

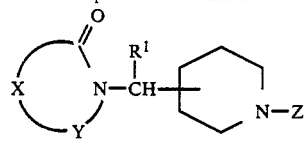

| Ex. | R¹ | X | Y | Piperidine Ring-link | Z | Formula[a] | m.p. (°) |
|---|---|---|---|---|---|---|---|
| 14 | H | —C₂H₄— | CH₂ | 4- | 3-Cl-pyridin-5-yl (N, Cl) | $C_{14}H_{19}ClN_4O$ | 141–142.5 |
| 15 | H | —C₂H₄— | CH₂ | 4- | 2-Cl, 5-CH₃ pyrimidinyl | $C_{15}H_{21}ClN_4O$ | 133–135 |
| 16 | H | —C₂H₄— | CH₂ | 4- | Cl, CH₃ substituted pyrimidinyl | $C_{15}H_{21}ClN_4O$ | 104–107 |
| 17 | H | —C₂H₄— | CH₂ | 4- | Br-pyrimidinyl | $C_{14}H_{19}BrN_4O$ | 143–146 |
| 18 | H | —C₂H₄— | CH₂ | 4- | Cl-pyrimidinyl | $C_{14}H_{19}ClN_4O$ | 130–133 |
| 19 | H | —C₂H₄— | CH₂ | 4- | I-pyrimidinyl | $C_{14}H_{19}IN_4O$ | 129.5–131.5 |
| 20 | H | —C₂H₄— | CH₂ | 4- | 2-SMe, 4-Cl pyrimidinyl | $C_{15}H_{21}ClN_4OS$ | 134–137 |
| 21 | H | —C₂H₄— | CH₂ | 4- | 3,5-diCl pyridazinyl | $C_{14}H_{18}Cl_2N_4O$ | 135–138 |
| 22 | H | —C₂H₄— | CH₂ | 4- | 2-Cl, 5-Br pyrimidinyl | $C_{14}H_{18}BrClN_4O$ | 105–115 |

TABLE 1-continued

Compounds of Formula I

| Ex. | R¹ | X | Y | Piperidine Ring-link | Z | Formula[a] | m.p. (°) |
|---|---|---|---|---|---|---|---|
| 23 | H | —C$_2$H$_4$— | CH$_2$ | 4- | pyrimidin-2-yl, OMe | C$_{15}$H$_{22}$N$_4$O | 116–121 |
| 24 | H | —C$_2$H$_4$— | CH$_2$ | 4- | pyrimidin-2-yl, CN | C$_{15}$H$_{19}$N$_5$O 0.2H$_3$O | 139.5–142 |
| 25 | H | 1,2-C$_6$H$_4$ | CH$_2$ | 4- | pyrimidin-2-yl | C$_{18}$H$_{20}$N$_4$O | 176–178 |
| 26 | H | —C$_2$H$_4$— | CH$_2$ | 4- | pyrimidin-2-yl, C$_2$F$_3$ | C$_{16}$H$_{19}$F$_5$N$_4$O | 105–107.5 |
| 27 | H | —C$_2$H$_4$— | CH$_2$ | 4- | pyrimidin-2-yl, CF$_3$, Cl | C$_{15}$H$_{18}$ClF$_3$N$_4$O | 102–104.5 |
| 28 | H | —C$_2$H$_4$— | CH$_2$ | 4- | pyrimidin-2-yl, CF$_3$, CF$_3$ | C$_{16}$H$_{18}$F$_6$N$_4$O 0.075 H$_2$O | 132.5–134 |

[a] C, H, and N analyses were within +0.4% of the calculated value.

Example 29

Reversal of ECS-induced Amnesia for Step-Down Passive Avoidance Response

In the step-down passive avoidance procedure, rats are trained to remain immobile to avoid foot shock. Two control groups (n=36/group) were required; and ECS control and a sham-ECS control. ECS control animals were placed individually on a platform over an activated shock grid (0.8 mA) 30 min. after vehicle administration. The animals readily stepped down from the platform, immediately experienced the foot shock, and quickly learned to escape to the platform. An animal was considered to have acquired the passive avoidance response if it remained on the platform for 2 minutes without stepping down following foot shock delivery. Immediately after acquisition, the ECS control animals were delivered ECS via transcorneal electrodes at an intensity of 50 nA for 400 msec. The sham-ECS control animals were treated in a manner indentical to that described for the ECS controls, with the exception that current was not passed through the transcorneal electrodes. Both groups were administered a retention test 24 hours later. Animals were placed individually on the platform, and the latency to step down from the platform onto the unactivated shock grid was recorded; a given subject animal considered to have retained the passive avoidance response if it remained on the platform for 300 seconds without stepping down. Sham-ECS controls remain on the platform during this test, showing normal retention; ECS controls readily stepped down within 300 seconds, exhibiting a deficit in retention (i.e., amnesia).

Step-down latency scores were transformed into percent retention scores with 300 seconds equal 100% retention. The percent retention scores for all drugs groups were evaluated against both the ECS and sham-ECS control groups using Dunnett's test. A compound was considered to be active in this test if the mean retention score obtained from at least one dose group is both significantly greater than the ECS control group retention and not significantly different form the sham-ECS control group retention. This indicates that the test compound reversed the amnesia for the passive avoidance task induced by the ECS. The compounds which statistically raised the animal's performance above that of the ECS control group, but did not raise the performance sufficiently to be not statistically different from the sham-ECS control group were scored as possessing "intermediate activity". These compounds, then, do statistically raise the animals' performance, but not sufficiently to give total protection against the amnesia.

The biological activities of selected Formula I compounds in the test outlined in Example 29 are given in Table 2.

TABLE 2

Biological Activities of Selected Formula I Compounds in Reversal of ECS-induced Amnesia for a Step-Down Passive Avoidance Response

| Ex. | Name | ECS-Induced Amnesia Reversal |
|---|---|---|
| — | pramiracetam (reference compound) | active[a] at 10 mg/kg s.c. |
| 1 | 2-[[1-(2-Pyrimidinyl)-4-piperidinyl]methyl]-1H—isoindole-1,3-(2H)-dione | active at 10 mg/kg s.c. |
| 2 | 1-[[1-(2-Pyrimidinyl)-4-piperidinyl]methyl]-2-pyrrolidinone | active at 10 mg/kg s.c. and p.o. |
| 3 | 1-[[1-(2-Chloro-4-pyrimidinyl)-4-piperidinyl]-methyl]-2-pyrrolidinone | active at 0.5 mg/kg s.c. and p.o. |
| 5 | 1-[[1-(6-Chloro-2-pyrazinyl)-4-piperidinyl]-methyl]-2-pyrrolidinone | active at 0.5 mg/kg s.c. |
| 6 | 1-[[1-[2-(Trifluoro-4-pyrimidinyl)-4-piperidinyl]-methyl]-2-pyrrolidinone | active at 0.25 to 10 mg/kg p.o., active at 0.5 to 10 mg/kg s.c. |
| 7 | 1-[[1-(2-Pyrimidinyl)-3-piperidinyl]methyl]-2-pyrrolidinone | active at 25 mg/kg s.c. |
| 8 | 1-[[1-(2-Pyrimidinyl)-2-piperidinyl]methyl]-2-pyrrolidinone | active at 25 mg/kg s.c. |
| 9 | 1-[[1-(6-Chloro-3-pyridazinyl)-4-piperidinyl]-methyl]-2-pyrrolidinone | active at 25 mg/kg s.c. |
| 10 | 1-[[1-(5-Fluoro-4-(methyl-thio)-2-pyrimidinyl]-4-piperidinyl]methyl]-2-pyrrolidinone | intermediate activity at 10 and 25 mg/kg s.c. |
| 11 | 1-[[1-(5-Fluoro-2-pyrimidinyl)-4-piperidinyl]-methyl]-2-pyrrolidinone | active at 10 mg/kg s.c. |
| 12 | 1-[[1-(2,6-Dichloro-4-pyrimidinyl)-4-piperidinyl]-methyl]-2-pyrrolidinone | active at 1.0 mg/kg s.c. |
| 13 | 1-[[1-(4,6-Dichloro-2-pyrimidinyl)-4-piperidinyl]methyl]-2-pyrrolidinone | Intermediate activity at 10 mg/kg s.c. |
| 14 | 1-[[1-(6-Chloro-4-pyrimidinyl)-4-piperidinyl]methyl]-2-pyrrolidinone | intermediate activity at 10 mg/kg s.c. |
| 15 | 1-[[1-(2-Chloro-6-methyl-4-pyrimidinyl)-4-piperidinyl]methyl]-2-pyrrolidinone | intermediate activity at 10 mg/kg s.c. |
| 17 | 1-[[1-(5-Bromo-2-pyrimidinyl)-4-piperidinyl]-methyl]-2-pyrrolidinone | active at 10 & 25 mg/kg p.o. |
| 18 | 1-[[1-(5-Chloro-2-pyrimidinyl)-4-piperidinyl]-methyl]-2-pyrrolidinone | active at 10 mg/kg p.o. |
| 19 | 1-[[1-(5-Iodo-2-pyrimidinyl)-4-piperidinyl]-methyl]-2-pyrrolidinone | active at 25 mg/kg p.o. |
| 22 | 1-[[1-(5-Bromo-2-chloro-4-pyrimidinyl)-4-piperidinyl]-methyl]-2-pyrrolidinone | active at 0.5-1.0 mg/kg p.o. |
| 23 | 1-[[1-(2-Methoxy-4-pyrimidinyl)-4-piperidinyl]-methyl]-2-pyrrolidinone | intermediate activity at 10 mg/kg p.o. |
| 24 | 4-[4-[(2-Oxopyrrolidin-1-yl)methyl]-1-piperidinyl]-2-pyrimidinecarbonitrile | active at 25 mg/kg p.o. |
| 26 | 1-[[1-[2-(Pentafluoroethyl)-4-pyrimidinyl-4-piperidinyl]methyl]-2-pyrrolidinone | intermediate activity at 10 mg/kg |
| 27 | 1-[[1-[5-Chloro-2-(trifluoromethyl)-4-pyrimidinyl]-4-piperidinyl]-methyl]-2-pyrrolidinone | intermediate activity at 10 mg/kg p.o. |
| 28 | 1-[[1-[2,6-bis(trifluoro-methyl)-4-pyrimidinyl]-4-piperidinyl]methyl]-2-pyrrolidinone | active at 10 mg/kg p.o. |

[a]"Active" denotes compounds which completely reversed the ECS-induced amnesia while "intermediate activity" denotes less than complete protection as described in Example 29

What is claimed is:

1. A compound selected from the group of 1,2-, 1,3-, and 1,4-disubstituted piperidine of Formula I

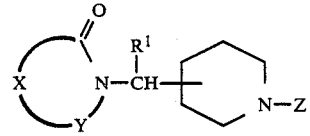

wherein
X is an ethylene chain or a 1,2-benzo ring;
Y is a carbonyl group or -CH$_2$-, with the proviso that Y is carbonyl only when X is a 1,2-benzo ring;
R$^1$ is selected from hydrogen or C$_{1-4}$alkyl; and
Z is an R$^2$-, R$^3$- disubstituted diazine bonded through a carbon atom thereof and selected from pyrimidine, pyridazine and pyrazine, with R$^2$ and R$^3$ being independently chosen from hydrogen, lower (C$_{1-4}$) alkyl, lower alkoxy, lower alkylthio, cyano, trifluoromethyl, pentafluorethyl, and halogen and connected at carbon atoms of the diazine;
and the pharmaceutically acceptable acid addition salts thereof.

2. A compound of claim 1 wherein X is ethylene and R$^1$ is hydrogen.

3. A compound of claim 1 wherein R$^2$ and R$^3$ are independently selected from hydrogen, halogen, and trifluoromethyl.

4. A compound of claim 2 wherein R$^2$ and R$^3$ are independently selected from hydrogen, halogen, and trifluoromethyl.

5. The compound of claim 1, 2-[[1-(2-pyrimidinyl)-4-piperidinyl]methyl]-1H-isoindole-1,3-(2H)-dione.

6. The compound of claim 1, 1-[[1-(2-pyrimidinyl)-4-piperidinyl)]methyl]-2-pyrrolidinone.

7. The compound of claim 1, 1-[[1-(2-chloro-4-pyrimidinyl) -4-piperidinyl]-methyl]-2-pyrrolidinone.

8. The compound of claim 1, 1-[[1-(4-chlro-2-pyrimidinyl) -4-piperidinyl]methyl]-2-pyrrolidinoine.

9. The compound of claim 1, 1-[[1-(6-chloro-2pyrazinyl)-4--piperidinyl]-methyl]-2-pyrrolidinone.

10. The compound of claim 1, 1-[[1-[2-(trifluoromethyl)-4-pyrimidinyl]methyl]-2-pyrrolidinone.

11. The compound of claim 1, 1-[[1-(2-pyrimidinyl)-3-piperidinyl]methyl]-2-pyrrolidinone.

12. The compound of claim 1, 1-[[1-2-pyrimidinyl)-2-piperidinyl]methyl]-2-pyrrolidinone.

13. The compound of claim 1, 1-[[1-(6-chloro-3-pyridazinyl)-4-piperidinyl]-methyl]-2-pyrrolidinone.

14. The compound of claim 1, 1-[[1-(5-fluoro-4-(methylthio)-2-pyrimidinyl]-4-piperidinyl]methyl]-2pyrrolidininone.

15. The compound of claim 1,1-[[1-(5-fluro-2-pyrimidinyl)-4-piperidinyl]-methyl]-2-pyrrolidinone.

16. The compound of claim 1, 1-[[1-(2,6-dichloro-4-pyrimidinyl)-4-piperidinyl]-methyl]-2-pyrrolidinone.

17. The compound of claim 1, 1-[[1-(4,6-dichloro-2-pyrimidinyl)-4-piperidinyl]methyl]-2-pyrrolidinone.

18. The compound of claim 1, 1-[[1-(6-chloro-4-pyrimidinyl)-b 4-piperidinyl]methyl]-2-pyrrolidinone.

19. The compound of claim 1, 1-[[1-(2-chloro-6-methyl-4-pyrimidinyl)-4-piperidinyl]methyl]-2-pyrrolidinone.

20. The compound of claim 1, 1-[[1-(4-chloro-6-methyl-2-pyrimidinyl)4-piperidinyl]methyl]-2-pyrrolidinone.

21. The compound of claim 1, 1[[1]-(5-bromo-2-pyrimidinyl)-4-piperidinyl]methyl]-2-pyrrolidinone.

22. The compound of claim 1, 1-[[1-(5-chloro-2-pyrimidinyl) -4-piperidinyl]methyl]-2-pyrrolidinone.

23. The compound of claim 1, 1[[-(5-iodo-2-pyrimidinyl)-4-piperidinyl]methyl]-2-pyrrolidinone.

24. The compound of claim 1, 1-[[1-(6-chloro-2-(methylthio)-4-pyrimidinyl]-4-piperdinyl]methyl]-2-pyrrolidinone.

25. The compound of claim 1, 1-[[1-(5,6-dichloro-4-pyridazinyl)-4-piperidinyl]methyl]-2-pyrrolidinone.

26. The compound of claim 1, 1-[[1-(5-bromo-2-chloro-4-pyrimidinyl)-4-piperidinyl]methyl]-2-pyrrolidinone.

27. The compound of claim 1, 1-[[1-(2-methyoxy-4-pyrimidinyl)-4-piperidinyl]methyl]-2-pyrrolidinone.

28. The compound of claim 1, 4-]4-(2-oxopyrrolidin-1-yl)methyl]-1-piperidinyl]-2-pyrimidine-carbonitrile.

29. The compound of claim 1, 1-[[1-]2-(pentafluoroethyl) -4-pyrimidinyl]-4-piperidinyl]methyl]2-pyrrolidinone.

30. The compound of claim 1, 1-[[1-[5-chloro-2-(trifluromethyl)-4-pyrimdinyl]-4-piperidinyl]methyl]2-pyrrolidinone.

31. The compound of claim 1, 1-[[1-[2,6-bis-trifluoromethyl)-4-pyurimidinyl]-4-piperidinyl]methyl]-2-pyrrolidinone.

32. The compound of claim 1, 1-[[1-(6-chloro-3-pyridazinyl) -4-piperidinyl]methhyl]-2-pyrrolidinone.

33. The method for enhancing cerebral function in a mammal in need of such treatment which comprises systemic administration to the mammal of an effective dose a compound claimed in claim 1.

34. The method for treating a disorder in a mammal in need of such treatment, the disorder selected from the group consisting of dementia, amnesia, failing memory, learning disability, mild retardation, dyslexia, aphasia, and Tourette's syndrome; the treatment comprising systemic administration to the mammal of an effective dose of a compound claimed in claim 1.

35. A compound of claim 1 comprising a 1,4-disubstituted piperidine of formula I.

36. A pharmaceutical composition for the enhancement of cerebral function comprising a pharmaceutical carrier and a compound according to claim 1.

* * * * *